United States Patent
Cerretti et al.

(10) Patent No.: US 6,596,852 B2
(45) Date of Patent: Jul. 22, 2003

(54) ANTIBODIES THAT BIND THE CYTOKINE DESIGNATED LERK-5

(75) Inventors: Douglas P. Cerretti, Seattle, WA (US); Pranhitha Reddy, Seattle, WA (US)

(73) Assignee: Immunex Corporation, Seattle, WA (US)

(*) Notice: Subject to any disclaimer, the term of this patent is extended or adjusted under 35 U.S.C. 154(b) by 101 days.

(21) Appl. No.: 09/978,339

(22) Filed: Oct. 15, 2001

(65) Prior Publication Data

US 2002/0103358 A1 Aug. 1, 2002

Related U.S. Application Data

(62) Division of application No. 08/271,948, filed on Jul. 8, 1994, now Pat. No. 6,303,769.

(51) Int. Cl.[7] ............ C07K 19/18; C12N 5/12; A61K 39/395

(52) U.S. Cl. ............... 530/387.9; 424/139.1; 424/141.1; 435/331; 530/387.1; 530/388.1; 530/389.1

(58) Field of Search ............. 435/331; 424/139.1, 424/141.1; 530/387.1, 387.9, 388.1, 389.1

(56) References Cited

U.S. PATENT DOCUMENTS

| | | |
|---|---|---|
| 5,134,121 A | 7/1992 | Mobley et al. |
| 5,512,457 A | 4/1996 | Lyman et al. |
| 5,516,658 A | 5/1996 | Beckmann et al. |
| 5,624,899 A | 4/1997 | Bennett et al. |
| 5,728,813 A * | 3/1998 | Lyman et al. |

FOREIGN PATENT DOCUMENTS

| | | |
|---|---|---|
| EP | 0 455 093 A2 | 11/1991 |
| EP | 0 597 503 A2 | 5/1994 |
| JP | 6/262882 | 10/1994 |
| JP | 6/320712 | 12/1994 |
| WO | WO 91/03569 | 3/1991 |
| WO | WO 92/07094 | 4/1992 |
| WO | WO 92/18112 | 10/1992 |
| WO | WO 93/00425 | 1/1993 |
| WO | WO 94/11384 | 5/1994 |
| WO | WO 96/02645 | 2/1996 |
| WO | WO 96/11212 | 4/1996 |

OTHER PUBLICATIONS

Cerretti et al., "Isolation of cDNAs that encode ligands to the receptor tyrosine kinases HEK and ELK: emergence of a family of proteins that are Ligands for the EPH Related Kinases (LERKS)," Abstract for American Assoc. for Cancer Research conference on Growth Factors, Development, and Cancer, Interlaken, Switzerland, Mar. 5–11, 1994.
Lyman et al., "Identification of a ligand for the ELK tyrosine kinase receptor," *Lymphokine Cytokine Res* vol. 12, No. 5, Abstract No. 92, Oct., 1993.
Beckmann et al., "Molecular characterization of a family of ligands for EPH–related tyrosine kinases," Abstract for Keystone Symposium on Inflammation, Growth Regulatory Molecules, and Atherosclerosis, Keystone, CO, Jan. 16–23, 1994.
Beal, M. F., "Role of excitotoxicity in human neurological disease," *Curr Opin Neurobiol* 2:657–662, 1992.
Choi, D. K., "Excitotoxic cell death," *J Neurobiol* 23:1261–1276, 1992.
Massieu et al., "A comparative analysis of the neuroprotective properties of competitive and uncompetitive N–methyl–D–aspartate receptor antagonists in vivo: implications for the process of excitotoxic degeneration and its therapy," *Neuroscience* 55:883–892, 1993.
Albin and Greenmyre, "Alternative excitotoxic hypothesis," *Neurology* 42:733–738, 1992.
Letwin et al., "Novel protein–tyrosine kinase cDNAs related to FPS/FES and EPH cloned using anti–phosphotyrosine antibody," *Oncogene* 3:621–627, 1988.
Lhotak et al., "Characterization of ELK, a brain–specific receptor tyrosine kinase," *Mol Cell Biol* 11:2496–2502, 1991.
Boyd et al., "Isolation and characterization of a novel receptor–type protein tyrosine kinase (HEK) from a human pre–B cell line," *J Biol Chem* 267:3262–3267, 1992.
Wicks et al., "Molecular cloning of HEK, the gene encoding a receptor tyrosine kinase expressed by human lymphoid tumor cell line," *Proc Natl Acad Sci USA* 89:1611–1615, 1992.
Sajjadi et al., "Identification of a new EPH–related receptor tyrosine kinase gene from mouse and chicken that is developmentally regulated and encodes at least two forms of the receptor," *New Biol* 3:769–788, 1991.
Chan and Watt, "EEK and ERK, new members of the EPH subclass of receptor protein–tyrosine kinases," *Oncogene* 6:1057–1061, 1991.
Lindberg et al., "cDNA cloning and characterization of ECK, an epithelial cell receptor protein–tyrosine kinase in the EPH/ELK family of protein kinases," *Mol Cell Biol* 10:6316–6324, 1990.
Pasquale, "Identification of chicken embryo kinase 5, a developmentally regulated receptor–type tyrosine kinase of the EPH family," *Cell Regulation* 2:523–534, 1991.
Hirai et al., "A novel putative tyrosine kinase receptor encoded by the EPH gene," *Science* 238:1717–1720, 1987.
Holzman et al., "A novel immediate–early response gene of endothelium is induced by cytokines and encodes a secreted protein," *Mol Cell Biol* 10:5830–5838, 1990.

(List continued on next page.)

*Primary Examiner*—Gary Kunz
*Assistant Examiner*—Stephen Gucker
(74) *Attorney, Agent, or Firm*—Randolph N. Mohr; Michael K. Kirschner; Stuart L. Watt

(57) ABSTRACT

LERK-5 polypeptides are disclosed, along with DNA sequences, vectors and transformed host cells useful in producing LERK-5. The LERK-5 polypeptides bind to elk and to hek, which are members of the eph/elk family of receptor tyrosine kinases.

16 Claims, No Drawings

OTHER PUBLICATIONS

Ashkenazi et al., "Protection against endotoxic shock by a tumor necrosis factor receptor immunoadhesin," *Proc Natl Acad Sci USA* 88:10535–10539, 1991.

Byrn et al., "Biological properties of a CD4 immunoadhesin," *Nature* 344:667–670, 1990.

Petrukhin et al., "A microsatellite genetic linkage map of human chromosome 13," *Genomics* 15:76–85, 1993.

Warburton et al., "Regional localization of 32 NotI–HindIII fragments from a human chromosome 13 library by a somatic cell hybrid panel and in situ hybridization," *Genomics* 16:355–360, 1993.

Brown et al., "Preliminary definition of a "critical region" of chromosome 13 in q32: report of 14 cases with 13q deletions and review of the literature," *Am J Med Gen* 45:52–59, 1993.

Bartley et al., "B61 is a ligand for the ECK receptor protein–tyrosine kinase," *Nature* 368:558–560, 1994.

Sakano et al., "Characterization of a ligand for receptor protein–tyrosine kinase HTK expressed in immature hematopoietic cells," *Oncogene* 13:813–822, 1996.

Bergemann et al., "ELF–2, a new member of the eph ligand family, is segmentally expressed in mouse embryos in the region of the hindbrain and newly forming somites," *Mol Cell Biol* 15(9):4921–4929, Sep. 1995.

Böhme et al., "Cell–cell adhesion mediated by binding of membrane–anchored ligand LERK–2 to the EPH–related receptor human embryonal kinase 2 promotes tyrosine kinase activity," *J Biol Chem* 271(40):24747–24752, Oct. 4, 1996.

Cerretti et al., "Ligands for the EPH–related kinases (LERKS) are developmentally regulated in the brain and are excito–protective for hippocampal neurons," *J Cell Biochem* Suppl. 21B, Abstract No. D3–100, Apr. 1995.

Böhme et al., "PCR mediated detection of a new human receptor–tyrosine–kinase HEK 2," *Oncogene* 8:2857–2862, 1993.

Schlom, "Monoclonal antibodies: they're more and less than you think," In *Molecular Foundations of Oncology*, Samuel Broder, ed., Williams & Wilkins, Baltimore, MD, pp. 95–134, 1991.

Bennett et al., "Molecular cloning of a ligand for the EPH–related receptor protein–tyrosine kinase htk," *Proc Natl Acad Sci USA* 92:1866–1870, Mar. 1995.

Cerretti et al., "Isolation of LERK–5: a ligand of the EPH–related receptor tyrosine kinases," *Mol Immunol* 32(16):1197–1205, 1995.

Bennett et al., "Molecular cloning of a ligand for the EPH–related receptor protein tyrosine kinase—HTK," *Blood* 84(10), Suppl. 1, p. 427a, Abstract No. 1693, Nov. 15, 1994.

* cited by examiner

ANTIBODIES THAT BIND THE CYTOKINE DESIGNATED LERK-5

CROSS REFERENCE TO RELATED APPLICATIONS

This application is a divisional of application Ser. No. 08/271,948, filed Jul. 8, 1994, which issued Oct. 16, 2001 as U.S. Pat. No. 6,303,769.

BACKGROUND OF THE INVENTION

Proteins known as the receptor tyrosine kinases have an intrinsic kinase activity that is activated upon ligand binding. This class of proteins is characterized by conserved structural motifs within the catalytic domains (Hanks et al., Science, 242:42, 1988) and can be subdivided into families based on structural features of the regions N-terminal to the catalytic domain.

Boyd et al. (J. Biol. Chem., 267:3262, 1992) purified a cell surface glycoprotein exhibiting tyrosine kinase activity. The N-terminal amino acid sequence identified this protein as a member of the eph/elk family, and the protein was thus designated hek (human eph/elk-like kinase). A monoclonal antibody immunoreactive with hek was used to study hek expression on a number of human cell types (Boyd et al., supra). Hek antigen was detected on the human pre-B cell leukemia cell line LK63 (the cell line employed as the immunogen against which the antibody was raised) and the human T-cell leukemia cell line JM. The Raji B lymphoma cell line showed weak hek antigen expression, and the remaining cell lines tested (both normal and tumor cell lines, among which were hemopoietic cell lines that included pre-B and T-cell lines) were consistently negative. Of the normal and tumor tissue biopsy specimens that were also tested for hek antigen expression, none of the normal tissues was positive and only a very low proportion of hemopoietic tumors was positive.

Expression of hek transcripts in the above-described LK63 and JM cell lines, as well as the human T-cell leukemia cell line HSB-2, has been demonstrated by northern blot analysis (Wicks et al., Proc. Natl. Acad. Sci. USA, 89:1611, 1992). Nucleotide and amino acid sequences for an isolated hek cDNA clone are presented in Wicks et al., supra.

The cell surface protein designated elk is another member of the tyrosine kinase receptor family of proteins. A partial clone of elk was first discovered in a rat brain cDNA expression library that was screened for proteins expressing tyrosine kinase activity (Letwin et al., Oncogene 3:621, 1988). Later, a composite sequence spanning the entire elk coding region was derived from partial clones isolated from a rat brain cDNA library and a rat cerebellar brain library using the partial clone as a probe (Lhotak et al., Mol. Cell. Biol. 11:2496, 1991).

The hek and elk proteins are closely related to a number of other receptor tyrosine kinases, including the hek homologs mek4 and cek4 (Sajjadi et al. New Biol. 3:769, 1991); eek (Chan et al. Oncogene 6:1057, 1991); erk (Chan et al. supra.), eck (Lindberg et al. Mol. Cell. Biol. 10:6316, 1990); cek5 (Pasquale, E. B. Cell Regulation 2:523, 1991); and eph (Hirai et al. Science 238:1717, 1987). The proteins of this subfamily are related not only in their cytoplasmic domains, but also in their extracellular domains, which are 41 to 68% identical. Interestingly, the tissue distributions of these various receptors are diverse. For example, expression of elk mRNA has been reported to be limited to testis and brain (Lhotak et al., supra), whereas eck is found not only in these same two tissues but in lung, intestine, kidney, spleen, ovary, and skin as well.

Those ligands that have been identified for the receptor tyrosine kinases are a diverse group of proteins that affect the growth, differentiation, and survival of cells expressing the receptors. Ligands for hek and elk have been isolated, as discussed in more detail below.

Identification of any additional ligands for hek and elk that may exist would prove useful in investigating the nature of cellular processes regulated by signaling through these receptors. If enhancement or inhibition of a particular biological signal mediated through these receptors is desired, it is advantageous to identify each of the proteins that may play a role in transduction of such signals. Further, proteins that bind to certain receptors without initiating signal transduction are known, including interleukin-l receptor antagonist protein (Eisenberg et al., Nature 343:341, 1990; Hannum et al., Nature 343:336, 1990; and Carter et al., Nature 344:633, 1990). Identification of any additional proteins that bind hek or elk is desirable in order to determine whether such proteins function as antagonists.

SUMMARY OF THE INVENTION

The present invention provides a novel cytokine designated LERK-5 that binds to elk and to hek, which are members of the eph/elk family of receptor tyrosine kinases. The present invention also provides isolated DNA encoding the LERK-5 protein and expression vectors comprising the isolated DNA. A method for producing LERK-5 comprises cultivating host cells containing the expression vectors under conditions appropriate for expression of LERK-5 protein, and recovering the LERK-5. Antibodies directed against the LERK-5 protein are also disclosed.

DETAILED DESCRIPTION OF THE INVENTION

A cDNA encoding a novel protein designated LERK-5, which binds to the cell surface receptors known as elk and hek, has been isolated in accordance with the present invention. Also provided are expression vectors comprising LERK-5 DNA. Methods for producing recombinant LERK-5 polypeptides involve cultivating host cells transformed with the expression vectors under conditions appropriate for expression of LERK-5, and recovering the expressed LERK-5. Purified LERK-5 protein is also encompassed by the present invention, including soluble forms of the protein comprising the extracellular domain.

The present invention also provides LERK-5 or fragments thereof that can act as immunogens to generate antibodies reactive therewith. In one embodiment, the antibodies are monoclonal antibodies specific for LERK-5.

Human LERK-5 cDNA was successfully isolated as described in example 1. The DNA sequence of the coding region of a human LERK-5 cDNA clone, and the amino acid sequence encoded thereby, are set forth in SEQ ID NO:1 and SEQ ID NO:2. The encoded protein comprises an N-terminal signal peptide (amino acids -25 to -1 of SEQ ID NO:2), an extracellular domain (amino acids 1 to 199), a transmembrane region (amino acids 200 to 225), and a cytoplasmic domain (amino acids 226 to 308). Binding of LERK-5 to the two cell surface receptors known as elk and hek is demonstrated in example 4.

A cell lysate containing a recombinant phage λgt10 vector comprising LERK-5 cDNA was deposited with the American Type Culture Collection on Jun. 16, 1994, and assigned accession no. ATCC 75815. The deposit was made under the terms of the Budapest Treaty. The recombinant λgt10 vector was that isolated in example I and identified as clone λ6.

The novel cytokine disclosed herein is a ligand for elk, a rat cell surface receptor that is a member of the eph/elk family of receptor tyrosine kinases. Expression of elk mRNA has been detected in the brain and testis of rats (Lhotok et al., supra), and the possibility that elk is capable of oncogenic activation has been suggested (Letwin et al., supra). The cytokine additionally is a ligand for hek, which is another member of the eph/elk family of receptor tyrosine kinases (Boyd et al., *J. Biol. Chem.*, 267:3262, 1992; Wicks et al., *PNAS USA*, 89:1611, 1992). Among the cell types on which hek is expressed are certain human leukemia cell lines.

The term "LERK-5" as used herein refers to a genus of polypeptides which are capable of binding elk and hek, and exhibit substantial homology to the LERK-5 amino acid sequences disclosed herein. Human LERK-5 is within the scope of the present invention, as are LERK-5 proteins derived from other mammalian species, including but not limited to murine, rat, bovine, porcine, or various primate species. As used herein, the term "LERK-5" includes membrane-bound proteins (comprising an extracellular domain, a transmembrane region, and a cytoplasmic domain) as well as truncated proteins that retain the elk-binding or hek-binding property. Such truncated proteins include, for example, soluble LERK-5 comprising only the extracellular (receptor binding) domain.

Other proteins that bind elk and hek have been identified. The LERK-5 of the present invention is a novel protein, distinct from these other elk-binding and hek-binding proteins.

One elk ligand is described in PCT application WO 94/11384. The nucleotide sequence of cloned cDNA (designated clone tele7) that encodes this elk ligand, as well as the amino acid sequence encoded thereby, are presented in WO 94/11384. The protein is a type 1 transmembrane protein comprising 346 amino acids, including an N-terminal signal peptide, an extracellular domain, a transmembrane domain, and a cytoplasmic domain.

Two hek ligand proteins (encoded by clones designated A2 and C6), which are 38% identical at the amino acid level, are described in U.S. Pat. No. 5,516,658. DNA and encoded amino acid sequences for cloned cDNA encoding the two hek ligand proteins are presented in U.S. Pat. No. 5,516,658. The encoded proteins each contain an N-terminal signal peptide, an extracellular domain, and a C-terminal hydrophobic region that contains signals for glycosyl-phosphatidylinositol (GPI) anchoring. After post-translational processing, both proteins are anchored to the cell surface via GPI linkage.

Another protein that has been found to bind elk and hek is designated B61. Nucleotide and encoded amino acid sequences for B61 cDNA are presented in Holzman et al. (*Mol. Cell. Biol.* 10:5830, 1990). B61 subsequently was found to bind elk and hek, as demonstrated in the binding assays described in U.S. Pat. No. 5,516,658.

Of these four proteins (B61 and the proteins encoded by clones tele7, A2, and C6), the LERK-5 of the present invention is most closely related (structurally) to the elk ligand encoded by tele7 (designated elk-L tele7 hereinafter). The amino acid sequences of the full length LERK-5 and elk-L tele7 proteins are 58.5% identical, and the DNA sequences are 61.4% identical. The sequences comprising the signal peptide and extracellular domain of elk-L and LERK-5 are 51.6% identical at the amino acid level, and 53.6% identical at the DNA level. The cytoplasmic domains are 74.7% identical at the amino acid level, and 75.5% identical at the DNA level.

The nucleotide sequence of a human expressed sequence tag (EST) for chromosome 13 is found in GenBank® under accession no. L13819. The source of the EST is identified as cDNA derived from mRNA from the brain of a 3-month old human female. When the 337 bp sequence disclosed for the EST is aligned with the elk-L tele7 nucleotide sequence, the sequence tag is 59.3% identical to the corresponding region of the elk-L tele7 DNA. In view of this degree of sequence homology, the present inventors sought to determine whether or not the sequence tag was part of a gene that encoded a biologically active protein, specifically, a protein that would bind elk or hek.

The GenBank record does not disclose any polypeptide encoded by the EST (e.g., does not indicate what the reading frame, if any, might be), much less suggest that any such polypeptide would bind elk or hek. Even if the sequence tag DNA were expressed in the reading frame elucidated by the cloning of LERK-5 DNA reported herein, the encoded amino acid sequence would lack three of the four cysteine residues that are conserved in the extracellular domains of the four above-described proteins that bind elk and hek. In the LERK-5 protein of the present invention, these cysteines are found at amino acids 37, 64, 76, and 128 of SEQ ID NO:2. A translate of the sequence tag would correspond to amino acids 79 to 190 of SEQ ID NO:2. Thus, the 337 bp sequence tag is not believed to encode a polypeptide capable of binding elk or hek.

The human LERK-5 cDNA isolated in example 1 below may be radiolabeled and used as a probe to isolate other mammalian LERK-5 cDNAs by cross-species hybridization. RNAs isolated from various cell lines or tissues derived from different mammalian species can be screened by Northern hybridization to identify a suitable source of mRNA for use in cloning a LERK-5 gene.

Fragments of the LERK-5 protein of SEQ ID NO:2 that are capable of binding elk or hek are encompassed by the present invention. One embodiment of the present invention provides soluble LERK-5 polypeptides. Soluble LERK-5 polypeptides comprise all or part of the extracellular domain of a native LERK-5 but lack the transmembrane region that would cause retention of the polypeptide on a cell membrane. Soluble LERK-5 polypeptides advantageously comprise the native (or a heterologous) signal peptide when initially synthesized to promote secretion, but the signal peptide is cleaved upon secretion of LERK-5 from the cell. The soluble LERK-5 polypeptides that may be employed retain the ability to bind elk or hek. Soluble LERK-5 may also include part of the transmembrane region or part of the cytoplasmic domain or other sequences, provided that the soluble LERK-5 protein is capable of being secreted.

Soluble LERK-5 may be identified (and distinguished from its non-soluble membrane-bound counterparts) by separating intact cells which express the desired protein from the culture medium, e.g., by centrifugation, and assaying the medium (supernatant) for the presence of the desired protein. The presence of LERK-5 in the medium indicates that the protein was secreted from the cells and thus is a soluble form of the desired protein. Soluble LERK-5 may be a naturally-occurring form of this protein.

The use of soluble forms of LERK-5 is advantageous for certain applications. Purification of the proteins from recombinant host cells is facilitated, since the soluble proteins are secreted from the cells. Further, soluble proteins are generally more suitable for intravenous administration.

Examples of soluble LERK-5 polypeptides include those comprising the entire extracellular domain of a native LERK-5 protein. One such soluble LERK-5 protein comprises amino acids 1 through 199 of SEQ ID NO:2. When initially expressed within a host cell, the soluble protein may additionally comprise one of the heterologous signal peptides described below that is functional within the host cells employed. Alternatively, the protein may comprise the native signal peptide, such that the LERK-5 comprises amino acids 25 through 199 of SEQ ID NO:2. DNA sequences encoding soluble LERK-5 proteins are encompassed by the present invention.

Truncated LERK-5, including soluble polypeptides, may be prepared by any of a number of conventional techniques. A desired DNA sequence may be chemically synthesized using known techniques. DNA fragments also may be produced by restriction endonuclease digestion of a full length cloned DNA sequence, and isolated by electrophoresis on agarose gels. Oligonucleotides that reconstruct the 5' or 3' end of a DNA fragment to a desired point may be synthesized. The oligonucleotide may contain a restriction endonuclease cleavage site upstream of the desired coding sequence and position an initiation codon (ATG) at the 5'-terminus of the coding sequence. Linkers containing restriction endonuclease cleavage site(s) may be employed to insert the desired DNA fragment into an expression vector. The well known polymerase chain reaction procedure also may be employed to isolate a DNA sequence encoding a desired protein fragment. Oligonucleotides that define the termini of the desired fragment are employed as primers in the PCR. As a further alternative, known mutagenesis techniques may be employed to insert a stop codon at a desired point, e.g., immediately downstream of the codon for the last amino acid of the extracellular domain.

Regarding the foregoing discussion of signal peptides and the various domains of the LERK-5 protein, the skilled artisan will recognize that the above-described boundaries of such regions of the protein are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, the exact boundaries of a transmembrane region may differ from those predicted by a computer program. Post-translational processing, which can vary according to the particular expression system employed, may yield proteins having N- or C-terminal amino acids that differ from those described above. Such variants that retain the desired biological activity are included among the LERK-5 polypeptides of the present invention.

The present invention provides purified LERK-5 polypeptides, both recombinant and non-recombinant. Variants and derivatives of native LERK-5 proteins that retain the desired biological activity (e.g., the ability to bind elk or hek) are also within the scope of the present invention. LERK-5 variants may be obtained by mutations of nucleotide sequences coding for native LERK-5 polypeptides. A LERK-5 variant, as referred to herein, is a polypeptide substantially homologous to a native LERK-5, but which has an amino acid sequence different from that of a native LERK-5 due to one or more deletions, insertions or substitutions.

A variant nucleotide or amino acid sequence preferably is at least 80% identical to a native LERK-5 sequence, most preferably at least 90% identical. In one embodiment of the present invention, a LERK-5 protein comprises an extracellular domain, a transmembrane region, and a cytoplasmic domain, wherein the amino acid acid sequence of said LERK-5 protein is at least 90% identical to the sequence presented as amino acids 1 to 308 of SEQ ID NO:2. In another embodiment, a soluble LERK-5 polypeptide capable of binding elk and hek comprises an amino acid sequence that is at least 90% identical to the sequence presented as amino acids 1 to 199 of SEQ ID NO:2.

The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

LERK-5 also may be modified to create LERK-5 derivatives by forming covalent or aggregative conjugates with other chemical moieties, such as glycosyl groups, lipids, phosphate, acetyl groups and the like. Covalent derivatives of LERK-5 may be prepared by linking the chemical moieties to functional groups on LERK-5 amino acid side chains or at the N-terminus or C-terminus of a LERK-5 polypeptide or the extracellular domain thereof. Other derivatives of LERK-5 within the scope of this invention include covalent or aggregative conjugates of LERK-5 or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a LERK-5 polypeptide. The signal or leader peptide co-translationally or post-translationally directs transfer of the conjugate from its site of synthesis to a site inside or outside of the cell membrane or cell wall.

LERK-5 polypeptide fusions can comprise peptides added to facilitate purification and identification of LERK-5. Such peptides include, for example, poly-His or the antigenic identification peptides described in U.S. Pat. No. 5,011,912 (hereby incorporated by reference) and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:3), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing.

The present invention further includes LERK-5 polypeptides with or without associated native-pattern glycosylation. LERK-5 expressed in yeast or mammalian expression systems (e.g., COS-7 cells) may be similar to or significantly different from a native LERK-5 polypeptide in molecular weight and glycosylation pattern, depending upon the choice of expression system. Expression of LERK-5 polypeptides in bacterial expression systems, such as *E. coli*, provides non-glycosylated molecules.

N-glycosylation sites in the LERK-5 extracellular domain can be modified to preclude glycosylation. Such sites in eukaryotic polypeptides are characterized by an amino acid triplet Asn-X-Y, wherein X is any amino acid except Pro and Y is Ser or Thr. The human LERK-5 protein comprises two such triplets, at amino acids 11–13 and 114–116 of SEQ ID NO:2. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg—Arg, Arg-Lys, and Lys-Arg pairs to eliminate the occurrence of these adjacent basic residues. Lys—Lys pairings are considerably less susceptible to KEX2 cleavage, and conversion of Arg-Lys or Lys-Arg to Lys—Lys represents a conservative and preferred approach to inactivating KEX2 sites. Human LERK-5 contains four KEX2 protease processing sites, at amino acids 228–229, 229–230, 232–233, and 251–252 of SEQ ID NO:2.

Naturally occurring LERK-5 variants are also encompassed by the present invention. Examples of such variants are proteins that result from alternative mRNA splicing events or from proteolytic cleavage of the LERK-5 protein, wherein the elk-binding or hek-binding property is retained. Alternative splicing of mRNA may yield a truncated but biologically active LERK-5 protein, such as a naturally occurring soluble form of the protein, for example. Variations attributable to proteolysis include, for example, differences in the N- or C-termini upon expression in different types of host cells, due to proteolytic removal of one or more terminal amino acids from the LERK-5 protein (generally from 1–5 terminal amino acids).

Variants possessing the requisite ability to bind elk or hek may be identified by any suitable assay. Biological activity of a LERK-5 variant may be determined, for example, by analyzing the variant's ability to compete with LERK-5 for binding to elk or hek (i.e., in competition binding assays).

Competition binding assays can be performed using standard techniques. For example, radiolabeled LERK-5 can be used to compete with a LERK-5 variant to assay for binding to cell surface-bound elk or hek. Qualitative results can be obtained by competitive autoradiographic plate binding assays, or Scatchard plots may be utilized to generate quantitative results. Instead of intact cells, one could substitute soluble elk or hek bound to a solid phase (e.g., a soluble elk/Fc or hek/Fc fusion protein bound to a solid phase containing Protein A or Protein G) Another type of competitive binding assay utilizes radiolabeled soluble elk or hek, and intact cells expressing LERK-5.

The LERK-5 of the present invention also can be used in a binding assay to detect cells expressing elk or hek. For example, LERK-5 or the extracellular domain thereof can be conjugated to a detectable moiety such as a radionuclide, an enzyme that can catalyze a colorometric or fluorometric reaction, biotin or avidin. Cells to be tested for elk or hek expression are contacted with the labeled LERK-5. After incubation, unbound labeled LERK-5 is separated from the cells, and binding is measured using the detectable moiety.

One aspect of the present invention involves the use of LERK-5 to bind elk or hek proteins. For example, LERK-5 may be employed as a reagent in protein purification procedures. LERK-5 or LERK-5/Fc fusion proteins are attached to a solid support material by conventional techniques and used to purify elk or hek by affinity chromatography.

The LERK-5 proteins disclosed herein also may be employed to measure the biological activity of elk or hek proteins in terms of their binding affinity for LERK-5. As one example, LERK-5 may be used in determining whether biological activity is retained after modification of an elk or hek protein (e.g., chemical modification, truncation, mutation, etc.). The biological activity of an elk or hek protein thus can be ascertained before it is used in a research study, for example.

LERK-5 proteins find use as reagents that may be employed by those conducting "quality assurance" studies, e.g., to monitor shelf life and stability of elk protein under different conditions. To illustrate, LERK-5 may be employed in a binding affinity study to measure the biological activity of an elk protein that has been stored at different temperatures, or produced in different cell types. The binding affinity of the modified elk protein for LERK-5 is compared to that of an unmodified elk protein to detect any adverse impact of the modifications on biological activity of elk. Likewise, the biological activity of a hek protein can be assessed using LERK-5.

LERK-5 polypeptides also find use as carriers for delivering agents attached thereto to cells bearing the elk or hek cell surface receptor. Expression of hek antigen has been reported for certain leukemic cell lines, including the human T-cell leukemia cell line designated JM and the human pre-B cell leukemia cell line designated LK63 (Boyd et al., *J. Biol. Chem.* 267:3262, 1992, and Wicks et al., *Proc. Natl. Acad. Sci. USA*, 89:1611, 1992). LERK-5 proteins thus can be used to deliver diagnostic or therapeutic agents to these cells (or to other cell types found to express hek on the cell surface) in in vitro or in vivo procedures.

One example of such use is to expose a hek$^+$ leukemic cell line to a therapeutic agent/LERK-5 conjugate to assess whether the agent exhibits cytotoxicity toward the leukemia cells. A number of different therapeutic agents attached to LERK-5 may be included in an assay to detect and compare the cytotoxic effect of the agents on the leukemia cells. LERK-5/diagnostic agent conjugates may be employed to detect the presence of hek$^+$ cells in vitro or in vivo.

Diagnostic and therapeutic agents that may be attached to a LERK-5 polypeptide include, but are not limited to, drugs, toxins, radionuclides, chromophores, enzymes that catalyze a calorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, Pseudomonas aeruginosa exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the LERK-5 by any suitable conventional procedure. LERK-5, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to LERK-5 by using a suitable bifunctional chelating agent, for example.

Conjugates comprising LERK-5 and a suitable diagnostic or thrapeutic agent (preferably covalently linked) are thus prepared. The conjugates are administered or otherwise employed in an amount appropriate for the particular application.

Another use of the LERK-5 of the present invention is as a research tool for studying the role that LERK-5, in conjunction with elk or hek, may play in growth or differentiation of cells bearing the elk or hek receptor. The LERK-5 polypeptides of the present invention also may be employed in in vitro assays for detection of elk or LERK-5 or the interactions thereof. Likewise, LERK-5 finds use in assays for hek or the interaction of LERK-5 with hek.

As discussed above, when various rat tissues were analyzed for elk mRNA, transcripts were detected only in brain and testis (Lhotak et al., supra). Binding of LERK-5 to elk on neural tissue is believed to exert a neuroprotective or neurotrophic effect.

LERK-5 finds use as a tissue culture reagent. A LERK-5 protein can be added to neurons cultured in vitro to enhance the viability or prolong the lifespan of the cultured neurons, thus facilitating research studies of neural tissue.

One embodiment of the present invention is directed to a method of treating disorders of neural tissue, involving contacting the neural tissue with LERK-5. Such disorders include injury or neurologic diseases, either chronic or acute. A LERK-5 protein may be administered to a mammal to treat such an injury or disease. In one embodiment of the invention, LERK-5 is employed in treating neurodegenerative conditions characterized or mediated, at least in part, by the mechanism of neural death known as excitotoxicity. In addition, LERK-5 may be administered to a mammal to exert a trophic effect on neural tissue. In a patient suffering loss of or damage to neurons due to injury or disease, LERK-5 may enhance the viability of those neurons that have survived.

The present invention provides pharmaceutical compositions comprising an effective amount of a purified LERK-5 polypeptide and a suitable diluent, excipient, or carrier. Such carriers will be nontoxic to patients at the dosages and concentrations employed. Ordinarily, the preparation of such compositions entails combining a mammalian LERK-5 polypeptide or derivative thereof with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent.

For therapeutic use, the compositions are administered in a manner and dosage appropriate to the indication and the patient. As will be understood by one skilled in the pertinent field, a therapeutically effective dosage will vary according to such factors as the nature and severity of the condition to be treated, and the age, size, and condition of the patient. Administration may be by any suitable route, including but not limited to continuous infusion, local infusion during surgery, intraventricular infusion (which may involve use of an intraventricular catheter), sustained release from implants (gels, membranes, and the like), or injection (e.g., injection at the site of an injury or injection into the central nervous system).

The compositions of the present invention may contain a LERK-5 protein in any form described above, including variants, derivatives, and biologically active fragments thereof. In one embodiment of the invention the composition comprises a soluble human LERK-5 protein. Such protein may comprise the extracellular domain of human LERK-5 fused to an Fc polypeptide, as described above.

Oligomeric Forms of LERK-5

Encompassed by the present invention are LERK-5 polypeptides in the form of oligomers, such as dimers or trimers. Such oligomers may be naturally occurring or produced by recombinant DNA technology. Oligomers may comprise LERK-5 polypeptides (preferably the extracellular domain or a fragment thereof) linked by disulfide bonds or expressed as a fusion protein with or without spacer peptide linkers. Oligomers may be formed by disulfide bonds between cysteine residues on different LERK-5 polypeptides, for example.

LERK-5 oligomers may be prepared using polypeptides derived from immunoglobulins. Preparation of fusion proteins comprising heterologous polypeptides fused to various portions of antibody-derived polypeptides (including the Fc domain) has been described, e.g., by Ashkenazi et al., (*PNAS USA* 88:10535, 1991) and Byrn et al., (*Nature* 344:677, 1990), hereby incorporated by reference. In one embodiment of the invention, a LERK-5 dimer is created by fusing LERK-5 to the Fc region of an antibody (IgG1). The Fc polypeptide preferably is fused to the C-terminus of a soluble LERK-5 (comprising only the extracellular domain). A gene fusion encoding the LERK-5/Fc fusion protein is inserted into an appropriate expression vector. The LERK-5/Fc fusion protein is expressed in host cells transformed with the recombinant expression vector, and allowed to assemble much like antibody molecules, whereupon interchain disulfide bonds form between Fc polypeptides, yielding divalent LERK-5. If fusion proteins are made with both heavy and light chains of an antibody, it is possible to form a LERK-5 oligomer with as many as four LERK-5 extracellular regions.

The term "Fc polypeptide" as used herein includes native and mutein forms of polypeptides derived from the Fc region of an antibody. Truncated froms of such polypeptides containing the hinge region that promotes dimerization are also included. One suitable Fc polypeptide, described in PCT application WO 93/10151, is a single chain polypeptide extending from the N-terminal hinge region to the native C-terminus. A mutein of this Fc polypeptide is described in example 3 below. The mutein exhibits reduced affinity for Fc receptors.

Alternatively, one can join LERK-5 polypeptides (preferably two soluble LERK-5 polypeptides) via a peptide linker. Peptide linkers suitable for joining polypeptides are known, and may be employed by conventional techniques. Fusion proteins comprising LERK-5 polypeptides joined by peptide linkers may be produced by recombinant DNA technology, for example.

The present invention provides oligomers of LERK-5 extracellular domains or fragments thereof, linked by disulfide interactions, or expressed as fusion polymers with or without spacer amino acid linking groups. For example, a dimer of the LERK-5 extracellular domain can be linked by an IgG Fc region linking group.

Expression Systems

The present invention provides recombinant expression vectors for expression of LERK-5, and host cells transformed with the expression vectors. Any suitable expression system may be employed. The vectors include a LERK-5 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the LERK-5 DNA sequence. Thus, a promoter nucleotide sequence is operably linked to a LERK-5 DNA sequence if the promoter nucleotide sequence controls the transcription of the LERK-5 DNA sequence. The ability to replicate in the desired host cells, usually conferred by an origin of replication, and a selection gene by which transformants are identified, may additionally be incorporated into the expression vector.

In addition, sequences encoding appropriate signal peptides that are not native to the LERK-5 gene can be incorporated into expression vectors. For example, a DNA sequence for a signal peptide (secretory leader) may be fused in frame to the LERK-5 sequence so that the LERK-5 is initially translated as a fusion protein comprising the signal peptide. A signal peptide that is functional in the intended host cells enhances extracellular secretion of the LERK-5 polypeptide. The signal peptide is cleaved from the LERK-5 polypeptide upon secretion of LERK-5 from the cell.

Suitable host cells for expression of LERK-5 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce LERK-5 polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a LERK-5 polypeptide may include an N-terminal methionine residue to facilitate expression of the recombinant polypeptide in the prokaryotic host cell. The N-terminal Met may be cleaved from the expressed recombinant LERK-5 polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a LERK-5 DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (*Maniatis, Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9 (ATCC 37092)) and pPLc28 (resident in *E. coli* RR1 (ATCC 53082)).

LERK-5 alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.*

255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the LERK-5 polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant LERK-5 polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566. Other suitable vectors may be derived from retroviruses.

In place of the native signal sequence, a heterologous signal sequence may be added, such as the signal sequence for interleukin-7 (IL-7) described in U.S. Pat. No. 4,965, 195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

LERK-5 Protein

The present invention provides purified LERK-5 protein, which may be produced by recombinant expression systems as described above or purified from naturally occurring cells. Advantageously, the LERK-5 is purified such that no protein bands corresponding to other proteins are detectable upon analysis by SDS-polyacrylamide gel electrophoresis (SDS-PAGE). It will be appreciated by one skilled in the pertinent field that multiple bands corresponding to LERK-5 protein may be visualized by SDS-PAGE, due to differential glycosylation, differential post-translational processing, and the like, as discussed above. The LERK-5 protein is considered to be purified as long as no bands corresponding to different (non-LERK-5) proteins are visualized. The LERK-5 most preferably is purified to substantial homogeneity, as indicated by a single protein band upon analysis by SDS-PAGE.

One process for producing the LERK-5 protein comprises culturing a host cell transformed with an expression vector comprising a DNA sequence that encodes LERK-5 under conditions such that LERK-5 is expressed. The LERK-5 protein is then recovered from culture medium or cell extracts, depending upon the expression system employed. As the skilled artisan will recognize, procedures for purifying the recombinant LERK-5 will vary according to such factors as the type of host cells employed and whether or not the LERK-5 is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify LERK-5. Some or all of the foregoing purification steps, in various combinations, can be employed to provide a substantially homogeneous recombinant protein.

It is also possible to utilize an affinity column comprising the ligand binding domain of elk or hek to affinity-purify expressed LERK-5 polypeptides. LERK-5 polypeptides can be recovered from an affinity column in a high salt elution buffer and then dialyzed into a lower salt buffer for use. Alternatively, an immunoaffinity column may comprise an antibody that binds LERK-5. Soluble LERK-5/Fc fusion proteins may be purified using a chromatography matrix having Protein A or Protein G attached thereto.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

In transformed yeast host cells, LERK-5 is preferably expressed as a secreted polypeptide to simplify purification. The secreted recombinant polypeptide can be purified by methods analogous to those disclosed by Urdal et al. (*J. Chromatog.* 296:171, 1984). Urdal et al. describe a procedure that includes two sequential, reversed-phase HPLC steps for purification of recombinant human IL-2 on a preparative HPLC column.

Nucleic Acids

The present invention further provides LERK-5 nucleotide sequences. Such nucleotide sequences include, but are not limited to, the LERK-5 DNA disclosed herein, in both single-stranded and double-stranded form, as well as the RNA complement thereof. LERK-5 DNA of the present invention includes, for example, cDNA, genomic DNA, chemically synthesized DNA, DNA amplified by PCR, and combinations thereof. Genonic DNA may be isolated by conventional techniques using the cDNA isolated in example 1, or a suitable fragment thereof, as a probe.

Examples of LERK-5 DNAs of the present invention include, but are not limited to, DNA comprising a nucleotide sequence selected from the group consisting of nucleotides 1 to 1002 of SEQ ID NO:1 (encoding the full length LERK-5 of SEQ ID NO:2); nucleotides 76 to 1002 of SEQ ID NO:1 (encoding a full length mature LERK-5); nucleotides 1 to 672 of SEQ ID NO:1 (encoding the signal peptide and extracellular domain); and nucleotides 76 to 672 of SEQ ID NO:1 (encoding the extracellular domain). Due to the known degeneracy of the genetic code, more than one codon can encode the same amino acid. Thus, a DNA sequence may vary from those described above, yet encode a polypeptide having the same amino acid sequence. Such variant DNA sequences may result from silent mutations, e.g., that may occur during PCR amplification. Alternatively, such silent mutations may be the product of deliberate mutagenesis of a native sequence. DNA sequences that are degenerate as a result of the genetic code to a LERK-5-encoding DNA sequence disclosed herein are encompassed by the present invention.

Useful fragments of the LERK-5 nucleic acids include antisense or sense oligonucleotides comprising a single-stranded nucleic acid sequence (either RNA or DNA) capable of binding to target LERK-5 mRNA (sense) or LERK-5 DNA (antisense) sequences. Antisense or sense oligonucleotides, according to the present invention, comprise a fragment of the coding region of LERK-5 cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of LERK-5 proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91104753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid

EXAMPLE 1

Isolation of Human LERK5 cDNA cDNA encoding human LERK5 was isolated as follows. The procedure began with preparation of a probe to use in identifying suitable cDNA libraries for use in the cloning attempt, and for screening those libraries.

First strand cDNA was synthesized on RNA isolated from a variety of cell types. Polymerase chain reactions (PCR) then were conducted by conventional techniques, using the cDNAs as templates. The 5' and 3' primers employed in the PCR were oligo-nucleotides that define the termini of a 337bp DNA fragment designated ch13 seq tag (GenBank® accession no. L13819). This DNA fragment was chosen in view of its degree of homology with a portion of an elk ligand DNA, as discussed in more detail above.

A DNA band of the expected size (337bp) was amplified by PCR in a reaction in which the cDNA template was derived from RNA isolated from a human T-cell leukemia cell line designated CCRF-HSB-2 (ATCC CCL 120.1). This 337bp single stranded DNA fragment (which consists of nucleotides 310 to 646 of SEQ ID NO:1) was isolated and labeled with $^{32}$P by standard techniques for use as a probe.

Northern blots containing mRNA from a variety of tissues were probed with the $^{32}$P-labeled DNA fragment. Hybridizing mRNA (about 5kb) was detected in tissues that included human fetal brain and lung. In addition, DNA bands of the expected size (337bp) were successfully amplified by PCR using either human adult or fetal lung cDNA libraries as the template. Thus, cDNA libraries derived from human fetal brain and from human lung fibroblasts were chosen for screening with the $^{32}$P-labeled probe in an effort to isolate a full length clone.

The human fetal brain cDNA library in the phage λ vector λgt10 was purchased from Clontech Laboratories, Inc., Palo Alto, Calif. The cDNA is inserted into the EcoRI site of the vector. The second cDNA library was derived from the SV40-transformed human adult lung fibroblast cell line WI-26 VA4. This library, in phage λ vector λgt10 was constructed as described in example 2 of U.S. Pat. No. 5,264,416, which is hereby incorporated by reference.

Screening with the 337bp probe was conducted by conventional procedures, and hybridizing clones were identified in both libraries. The nucleotide sequence of the cDNA insert of one individual clone isolated from the human fetal brain library, designated clone λ6, was determined. The DNA sequence of the coding region of the clone λ6 cDNA, and the amino acid sequence encoded thereby, are presented in SEQ ID NO:1 and SEQ ID NO:2. A clone isolated from the WI26 VA4 library comprised DNA truncated at the 5' end, but only 5bp short of the initiation codon of the sequence of SEQ ID NO:1.

The encoded protein, designated LERK-5, comprises an N-terminal signal peptide (amino acids -25 to -1 of SEQ ID NO:2), an extracellular domain (amino acids 1 to 199), a transmembrane region (amino acids 200 to 225), and a cytoplasmic domain (amino acids 226 to 308). LERK-5 binds to the two cell surface receptors known as elk and hek, as demonstrated in example 4.

A cell lysate containing clone λ6 DNA (the LERK-5 cDNA in λgt10) was deposited with the American Type Culture Collection, Rockville, Md., USA on Jun. 16, 1994, and assigned accession number ATCC 75815. The deposit was made under the terms of the Budapest Treaty.

EXAMPLE 2

Preparation of Soluble elk/Fc Fusion Protein

This example describes construction of an expression vector encoding a soluble elk/Fc fusion protein. This fusion protein was employed in the binding assay of example 4, to determine whether LERK-5 is capable of binding elk.

A DNA and encoded amino acid sequence for rat elk cDNA is presented in Lhotak et al. (*Mol. Cell. Biol.* 11:2496, 1991), hereby incorporated by reference. The rat elk protein has a 538 amino acid extracellular domain, a 25 amino acid transmembrane domain, and a 419 amino acid cytoplasmic domain.

A rat elk cDNA fragment was fused to the 5' end of cDNA encoding the Fc portion of a human IgG1 antibody. The rat elk cDNA was obtained from T. Pawson (Samuel Lunenfeld Research Institute, Mt. Sinai Hospital, Toronto). An Asp718 restriction endonuclease cleavage site was introduced upstream of the elk coding region. An Asp 718-BglII fragment of rat elk cDNA (comprising the entire extracellular domain, the transmembrane region, and a small portion of the cytoplasmic domain) was isolated.

DNA encoding a single polypeptide chain comprising the Fc region of a human IgG1 antibody was cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. The nucleotide sequence of the cloned DNA, along with the amino acid sequence of the Fc polypeptide encoded thereby, are described in PCT application WO 93/10151, hereby incorporated by reference. A unique BglII site has been introduced, and encompasses the codons for amino acids three and four of the Fc polypeptide. The encoded Fc polypeptide extends from the N-terminal hinge region to the native C-terminus, i.e., is an essentially full-length antibody Fc region.

The above-described Asp718-BglII elk cDNA fragment was cloned into the pBLUESCRIPT SK® vector containing the Fc cDNA, such that the elk cDNA is positioned upstream of the Fc cDNA. Single stranded DNA derived from the resulting gene fusion was mutagenized by the method described in Kunkel (*Proc. Natl. Acad. Sci. USA* 82:488, 1985) and Kunkel et al. (*Methods in Enzymol.* 154:367, 1987) in order to perfectly fuse the entire extracellular domain of elk to the Fc sequence. The mutagenized DNA was sequenced to confirm that the proper nucleotides had been removed (i.e., that the transmembrane region and partial cytoplasmic domain DNA were deleted) and that the elk and Fc sequences were in the same reading frame.

The elk/Fc fusion protein preferably is synthesized in mammalian host cells, such as CV1-EBNA or COS-7 cells. The elk/Fc gene fusion was excised and inserted into a mammalian expression vector designated HAV-EO (Dower et al., *J. Immunol.* 142:4314, 1989). Mammalian host cells were transfected with the resulting recombinant expression vector and cultivated to allow transient expression of the fusion protein, which was secreted into the culture medium via the elk signal peptide. The elk/Fc fusion protein was purified by affinity chromatography, using a protein A sepharose column.

EXAMPLE 3

Preparation of Soluble hek/Fc Fusion Protein

This example describes construction of an expression vector encoding a soluble hek/Fc fusion protein. This fusion protein was employed in the binding assays of example 4, to determine whether LERK-5 is capable of binding hek.

A DNA and encoded amino acid sequence for human hek cDNA is presented in Wicks et al. (*Proc. Nat'l. Acad. Sci. USA*, 89:1611, 1992), hereby incorporated by reference. This hek protein comprises (from N- to C-terminus) an extracellular domain, a transmembrane domain, and a cytoplasmic domain.

Two DNA fragments, one encoding an N-terminal fragment of the extracellular domain of hek and the other encoding a C-terminal fragment of the hek extracellular domain, were isolated by polymerase chain reactions (PCR) conducted under standard conditions, using oligonucleotide primers based on the hek nucleotide sequence published by Wicks et al., supra. The template for the PCR was cDNA prepared from mRNA isolated from a human T-cell leukemic cell line designated CCRF-HSB-2 (ATCC CCL-120.1). The PCR products containing the 5' end of the hek DNA were digested with SpeI and HindIII to isolate a DNA fragment extending from the 5' end of the mature human hek sequence (i.e., lacking DNA encoding the signal sequence) to a HindIII site found in the hek gene. The PCR products containing the 3' end of the hek extracellular domain DNA were digested with HindIII and ClaI to isolate a fragment extending from the internal HindIII site to a ClaI site just downstream of the 3' end of the sequence encoding the hek extracellular domain. The ClaI site is in a multiple cloning site (mcs) introduced just downstream of the extracellular domain.

DNA encoding a mutein of the Fc region of a human IgG1 antibody was isolated. This Fc mutein DNA and the polypeptide encoded thereby are described in U.S. Pat. No. 5,457,035, entitled "Novel Cytokine Which is a Ligand for OX40" filed Jul. 23, 1993, which application is hereby incorporated by reference. The mutein DNA was derived from a native Fc polypeptide-encoding DNA by site-directed mutagenesis conducted essentially as described by Deng and Nickoloff, *Anal. Biochem.* 200:81 (1992). The amino acid sequence of the Fc mutein polypeptide is identical to that of the native Fc polypeptide described in PCT application WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

A recombinant vector containing the Fc mutein DNA was cleaved with ClaI and NotI, which cleave the vector in a polylinker region immediately upstream and downstream, respectively, of the Fc mutein DNA insert. The desired Fc mutein-encoding fragment was isolated.

The mutein Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate hek/Fc fusion proteins, creating dimers.

A mammalian expression vector designated SMAG4 was cleaved with SpeI and NotI. The SMAG4 vector comprises a murine interleukin-7 signal peptide-encoding sequence (described in U.S. Pat. No. 4,965,195) inserted into the mammalian high expression vector pDC201 (described in Sims et al., *Science* 241:585, 1988, and in PCT application WO 89/03884), which is also capable of replication in *E. coli*. SpeI cleaves the vector immediately downstream of the IL-7 signal peptide-encoding sequence. NotI cleaves approximately 155 bp downstream of the SpeI site in a multiple cloning site of the vector. The large SpeI/NotI fragment containing the vector sequences and the IL-7 signal peptide-encoding DNA was isolated.

A four-way ligation was conducted to insert the two hek-encoding DNA fragments and the Fc mutein-encoding DNA fragment described above into the SpeI/NotI cleaved SMAG4 expression vector. *E. coli* cells were transfected with the ligation mixture and the desired recombinant vector was isolated therefrom. The isolated vector encodes a fusion protein comprising (from N- to C-terminus) the murine IL-7 signal peptide, the hek extracellular domain, four amino acids encoded by the introduced mcs, and the Fc mutein.

The expression vector was then co-transfected with plasmid pSV3.NEO into CV1/EBNA cells. The CV1/EBNA cell line (ATCC CRL 10478) was derived from a monkey kidney cell line as described in McMahan et al. (*EMBO J.*, 10:2821, 1991). Vector pSV3.NEO expresses SV40 T-antigen, which is not produced by the host cells. The pSV3.NEO vector is similar to pSV3 (Mulligan and Berg, *Proc. Natl. Acad. Sci. USA* 78:2072, 1981), but additionally contains a neomycin resistance gene. The transformed cells were cultivated to allow transient expression of the fusion protein, which is secreted into the culture medium via the murine IL-7 signal peptide. The fusion protein was purified on a protein A Sepharose column, eluted, and used to screen cells for the ability to bind the hek/Fc protein, as described in Examples 2 and 3.

EXAMPLE 4

Binding Study

The ability of LERK-5 to bind to the receptors known as elk and hek was investigated in the following assay. The procedure began with preparation of cells expressing LERK-5 on the cell surface.

LERK-5 DNA was amplified by PCR, using the clone λ6 DNA described in example 1 as the template. The primers employed in the PCR defined the termini of the coding region of the LERK-5 DNA, and also added a Xho I restriction site at the 5' end and a Not I site at the 3' end of the amplified DNA. The 5' primer additionally added a consensus Kozak sequence upstream of the initiation codon.

The reaction products were digested with Xho I and Not I and inserted into an expression vector cleaved with Sal I (which is compatible with Xho 1) and Not I. The expression vector is was pDC410, which is a mammalian expression vector that also replicates in *E. coli*. pDC410 is similar to pDC406 (McMahan et al., *EMBO J.* 10:2821, 1991). The pDC410 multiple cloning site (mcs) differs from that of pDC406 in that it contains additional restriction sites and three stop codons (one in each reading frame). A T7 polymerase promoter downstream of the mcs facilitates sequencing of DNA inserted into the mcs. In addition, the EBV origin of replication is replaced by DNA encoding the SV40 large T antigen (driven from an SV40 promoter) in pDC410.

CV1-EBNA-1 cells in 10 $cm^2$ dishes were transfected with the recombinant expression vector containing LERK-5 DNA. The CV-1/EBNA-1 cell line (ATCC CRL 10478)

constitutively expresses EBV nuclear antigen-I driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells were cultured for 24 hours, and the cells in each dish then were split into a 24-well plate. After culturing an additional 48 hours, a binding assay was conducted by the following procedure. The transfected cells (about $4 \times 10^4$ cells/well) were washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then were incubated for 1 hour at 37° C. with various concentrations of the elk/Fc fusion protein prepared in Example 2 or the hek/Fc fusion protein prepared in Example 3. Cells then were washed and incubated with a constant saturating concentration of a $^{125}$I-mouse anti-human IgG in binding medium, with gentle agitation for 1 hour at 37° C. After extensive washing, cells were released via trypsinization.

The mouse anti-human IgG employed above is directed against the Fc region of human IgG and was obtained from Jackson Immunoresearch Laboratories, Inc., West Grove, Pa. The antibody was radioiodinated using the standard chloramine-T method. The antibody will bind to the Fc portion of any elk/Fc or hek/Fc fusion protein that has bound to the cells. In all assays, non-specific binding of $^{125}$I-antibody was assayed in the absence of elk/Fc (or hek/Fc), as well as in the presence of elk/Fc (or hek/Fc) and a 200-fold molar excess of unlabeled mouse anti-human IgG antibody.

Cell-bound $^{125}$I-antibody was quantified on a Packard Autogamma counter. Affinity calculations (Scatchard, *Ann. N.Y. Acad. Sci.* 51:660, 1949) were generated on RS/1 (BBN Software, Boston, Mass.) run on a Microvax computer.

In the assay for binding elk/Fc, the cells expressing recombinant LERK-5 exhibited a single affinity class of binding, with approximately 103,317 binding sites per cell. The affinity constant ($K_A$) was $1.05 \times 10^9$ M$^{-1}$. The cells expressing recombinant LERK-5 were also found to bind hek/Fc.

EXAMPLE 5

Northern Blot Analyses

To investigate expression of LERK-5 in various tissues, Northern blots that contained mRNA from a variety of human tissues (both fetal and adult) were probed with a LERK-5 riboprobe. The riboprobe was derived from the 337 bp DNA fragment isolated in example 1, as follows.

Oligonucleotides that define the termini of the 337 bp DNA fragment were employed as primers in a polymerase chain reaction (PCR). The 3' primer additionally included the T3 RNA polymerase promoter. The PCR was carried out by conventional techniques, using the 337 bp DNA as the template. The resulting amplified DNA thus contained the T3 RNA polymerase promoter at the 3' end. A riboprobe was prepared by standard techniques, using T3 RNA polymerase and the amplified DNA as the template.

The blots were hybridized with the riboprobe at 63° C., then washed, first with 1× SSC/0.1% SDS for 1 h at 68° C., then with 0.1× SSC/0.1% SDS for 30 min at 68° C. The blot was exposed to X-ray film at −70° for 11 days sandwiched between two intensifying screens.

In the blot containing RNA derived from fetal tissues, a major mRNA band about 5.0 kb was visualized in heart, brain, lung, and kidney, but not in liver. In blots containing RNA from adult tissues, a 5kb band was detected in lung and kidney, although expression levels appeared lower than in the fetal tissues. A hybridizing mRNA band was not detectable, or was very faint, in adult heart, brain, placenta, liver, skeletal muscle, pancreas, spleen, thymus, prostate, testis, ovary, small intestine, colon and peripheral blood lymphocytes.

EXAMPLE 6

Monoclonal Antibodies to LERK-5

This example illustrates the preparation of monoclonal antibodies to LERK-5. LERK-5 is expressed in mammalian host cells such as COS-7 or CV-1/EBNA-1 cells and purified using elk/Fc affinity chromatography. Purified LERK-5 (or a fragment thereof such as the extracellular domain) can be used to generate monoclonal antibodies against LERK-5 using conventional techniques, for example, those techniques described in U.S. Pat. No. 4,411,993. Briefly, mice are immunized with LERK-5 as an immunogen emulsified in complete Freund's adjuvant, and injected in amounts ranging from 10–100 µg subcutaneously or intraperitoneally. Ten to twelve days later, the immunized animals are boosted with additional LERK-5 emulsified in incomplete Freund's adjuvant. Mice are periodically boosted thereafter on a weekly to bi-weekly immunization schedule. Serum samples are periodically taken by retro-orbital bleeding or tail-2p excision for testing by dot blot assay or ELISA (Enzyme-Linked Immunosorbent Assay), for LERK-5 antibodies.

Following detection of an appropriate antibody titer, positive animals are provided one last intravenous injection of LERK-5 in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified LERK-5 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-LERK-5 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to LERK-5.

What is claimed is:

1. A purified antibody that is immunoreactive with a LERK-5 polypeptide, with the proviso that said antibody does not specifically bind to elk-L tele7, wherein the LERK-5 polypeptide is encoded by the LERK-5 cDNA in the recombinant vector deposited as ATCC 75815.

2. An antibody according to claim 1, wherein said antibody is a monoclonal antibody.

3. A purified antibody that is specific for a LERK-5 polypeptide, with the proviso that said antibody does not specifically bind to elk-L tele7, wherein said LERK-5 polypeptide comprises an amino acid sequence selected from the group consisting of amino acids 1–308 of SEQ ID NO:2 and 1–199 of SEQ ID NO:2.

4. An antibody according to claim 3, wherein said antibody is polyclonal.

5. A purified antibody that is specific for a LERK-5 polypeptide, with the proviso that said antibody does not specifically bind to elk-L tele7, wherein said polypeptide is capable of binding elk or hek, wherein said LERIK-5 polypeptide comprises an amino acid sequence that is at least 90% identical (using the GAP computer program, version 6.0, with the preferred default parameters) to the sequence of residues 1–199 of SEQ ID NO:2.

6. An antibody according to claim 5, wherein said antibody is polyclonal.

7. A purified antibody that is specific for a LERK-5 polypeptide, with the proviso that said antibody does not specifically bind to elk-L tele7, wherein said polypeptide is capable of binding elk or hek, wherein said LERK-5 polypeptide comprises an extracellular domain, a transmembrane region, and a cytoplasmic domain, and wherein said LERK-5 polypeptide comprises an amino acid sequence that is at least 90% identical (using the GAP computer program, version 6.0, with the preferred default parameters) to the sequence of residues 1–308 of SEQ ID NO:2.

8. An antibody according to claim 7, wherein said antibody is polyclonal.

9. A method for producing a monoclonal antibody specific for a LERK-5 polypeptide, with the proviso that said antibody does not specifically bind to elk-L tele7, said method comprising the steps of:
   a) immunizing an animal with a LERK-5 polypeptide selected from the group consisting of the protein of SEQ ID NO:2 and an immunogenic fragment of the protein of SEQ ID NO:2;
   b) harvesting spleen cells from the immunized animal;
   c) fusing said spleen cells to a myeloma cell line, thereby generating hybridoma cells;
   d) identifying a hybridoma cell line that produces monoclonal antibodies specific for the LERK-5 polypeptide; and
   e) purifying monoclonal antibodies produced by said hybridoma cell line.

10. A method according to claim 9, comprising immunizing the animal with the protein of SEQ ID NO:2.

11. A method according to claim 9, comprising immunizing the animal with an immunogenic fragment comprising the extracellular domain of the protein of SEQ ID NO:2.

12. A monoclonal antibody produced by a method according to claim 9.

13. A method of producing a hybridoma cell line, said method comprising the steps of:
   a) immunizing an animal with a LERK-5 polypeptide selected from the group consisting of the protein of SEQ ID NO:2 and an immunogenic fragment of the protein of SEQ ID NO:2;
   b) harvesting spleen cells from said animal;
   c) fusing said spleen cells to a myeloma cell line, thereby generating hybridoma cells; and
   d) identifying a hybridoma cell line that produces monoclonal antibodies specific for the LERK-5 polypeptide, with the proviso that said antibodies do not specifically bind to elk-L tele7.

14. A method according to claim 13, comprising immunizing the animal with the protein of SEQ ID NO:2.

15. A method according to claim 13, comprising immunizing the animal with an immunogenic fragment comprising the extracellular domain of the protein of SEQ ID NO:2.

16. A method for producing an antibody, with the proviso that said antibody does not specifically bind to elk-L tele7, comprising immunizing an animal with a LERK-5 polypeptide selected from the group consisting of the protein of SEQ ID NO:2 and an immunogenic fragment of the protein of SEQ ID NO:2; whereby antibodies directed against the LERK-5 polypeptide are generated in said animal.

* * * * *

UNITED STATES PATENT AND TRADEMARK OFFICE
CERTIFICATE OF CORRECTION

PATENT NO. : 6,596,852 B2
DATED : July 22, 2003
INVENTOR(S) : Douglas P. Cerretti and Pranhitha Reddy It is certified that error appears in the above-identified patent and that said Letters Patent is hereby corrected as shown below:

Column 16,
Line 57, change "WO 91104753" to read -- WO 91/04753 --.

Column 17,
Line 33, change "(about Skb)" to read -- (about 5kb) --.
Line 42, change "X" to read -- λ --.
Line 59, change "Sbp" to read -- 5bp --.

Column 22,
Line 2, change "Skb" to read -- 5kb --.

Signed and Sealed this

Eighteenth Day of May, 2004

JON W. DUDAS
*Acting Director of the United States Patent and Trademark Office*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1002 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
      (B) CLONE: huLERK-5

(ix) FEATURE:
      (A) NAME/KEY: CDS
      (B) LOCATION: 1..1002

(ix) FEATURE:
      (A) NAME/KEY: sig_peptide
      (B) LOCATION: 1..75

(ix) FEATURE:
      (A) NAME/KEY: mat_peptide
      (B) LOCATION: 76..999

(xi) SEQUENCE DESCRIPTION: SEQ ID NO: 1:

```
ATG GCT GTG AGA AGG GAC TCC GTG TGG AAG TAC TGC TGG GGT GTT TTG        48
Met Ala Val Arg Arg Asp Ser Val Trp Lys Tyr Cys Trp Gly Val Leu
-25              -20                 -15                 -10

ATG GTT TTA TGC AGA ACT GCG ATT TCC AAA TCG ATA GTT TTA GAG CCT        96
Met Val Leu Cys Arg Thr Ala Ile Ser Lys Ser Ile Val Leu Glu Pro
                 -5                  1                5

ATC TAT TGG AAT TCC TCG AAC TCC AAA TTT CTA CCT GGA CAA GGA CTG       144
Ile Tyr Trp Asn Ser Ser Asn Ser Lys Phe Leu Pro Gly Gln Gly Leu
             10                  15                  20

GTA CTA TAC CCA CAG ATA GGA GAC AAA TTG GAT ATT ATT TGC CCC AAA       192
Val Leu Tyr Pro Gln Ile Gly Asp Lys Leu Asp Ile Ile Cys Pro Lys
        25                  30                  35

GTG GAC TCT AAA ACT GTT GGC CAG TAT GAA TAT TAT AAA GTT TAT ATG       240
Val Asp Ser Lys Thr Val Gly Gln Tyr Glu Tyr Tyr Lys Val Tyr Met
40                  45                  50                  55

GTT GAT AAA GAC CAA GCA GAC AGA TGC ACT ATT AAG AAG GAA AAT ACC       288
Val Asp Lys Asp Gln Ala Asp Arg Cys Thr Ile Lys Lys Glu Asn Thr
                60                  65                  70

CCT CTC CTC AAC TGT GCC AAA CCA GAC CAA GAT ATC AAA TTC ACC ATC       336
Pro Leu Leu Asn Cys Ala Lys Pro Asp Gln Asp Ile Lys Phe Thr Ile
            75                  80                  85

AAG TTT CAA GAA TTC AGC CCT AAC CTC TGG GGT CTA GAA TTT CAG AAG       384
Lys Phe Gln Glu Phe Ser Pro Asn Leu Trp Gly Leu Glu Phe Gln Lys
            90                  95                  100

AAC AAA GAT TAT TAC ATT ATA TCT ACA TCA AAT GGG TCT TTG GAG GGC       432
Asn Lys Asp Tyr Tyr Ile Ile Ser Thr Ser Asn Gly Ser Leu Glu Gly
        105                 110                 115

CTG GAT AAC CAG GAG GGA GGG GTG TGC CAG ACA AGA GCC ATG AAG ATC       480
Leu Asp Asn Gln Glu Gly Gly Val Cys Gln Thr Arg Ala Met Lys Ile
120                 125                 130                 135
```

```
CTC ATG AAA GTT GGA CAA GAT GCA AGT TCT GCT GGA TCA ACC AGG AAT          528
Leu Met Lys Val Gly Gln Asp Ala Ser Ser Ala Gly Ser Thr Arg Asn
            140                 145                 150

AAA GAT CCA ACA AGA CGT CCA GAA CTA GAA GCT GGT ACA AAT GGA AGA          576
Lys Asp Pro Thr Arg Arg Pro Glu Leu Glu Ala Gly Thr Asn Gly Arg
            155                 160                 165

AGT TCG ACA ACA AGT CCC TTT GTA AAA CCA AAT CCA GGT TCT AGC ACA          624
Ser Ser Thr Thr Ser Pro Phe Val Lys Pro Asn Pro Gly Ser Ser Thr
            170                 175                 180

GAC GGC AAC AGC GCC GGA CAT TCG GGG AAC AAC ATC CTC GGT TCC GAA          672
Asp Gly Asn Ser Ala Gly His Ser Gly Asn Asn Ile Leu Gly Ser Glu
            185                 190                 195

GTG GCC TTA TTT GCA GGG ATT GCT TCA GGA TGC ATC ATC TTC ATC GTC          720
Val Ala Leu Phe Ala Gly Ile Ala Ser Gly Cys Ile Ile Phe Ile Val
200                 205                 210                 215

ATC ATC ATC ACG CTG GTG GTC CTC TTG CTG AAG TAC CGG AGG AGA CAC          768
Ile Ile Ile Thr Leu Val Val Leu Leu Leu Lys Tyr Arg Arg Arg His
            220                 225                 230

AGG AAG CAC TCG CCG CAG CAC ACG ACC ACG CTG TCG CTC AGC ACA CTG          816
Arg Lys His Ser Pro Gln His Thr Thr Thr Leu Ser Leu Ser Thr Leu
            235                 240                 245

GCC ACA CCC AAG CGC AGC GGC AAC AAC AAC GGC TCA GAG CCC AGT GAC          864
Ala Thr Pro Lys Arg Ser Gly Asn Asn Asn Gly Ser Glu Pro Ser Asp
            250                 255                 260

ATT ATC ATC CCG CTA AGG ACT GCG GAC AGC GTC TTC TGC CCT CAC TAC          912
Ile Ile Ile Pro Leu Arg Thr Ala Asp Ser Val Phe Cys Pro His Tyr
            265                 270                 275

GAG AAG GTC AGC GGG GAC TAC GGG CAC CCG GTG TAC ATC GTC CAG GAG          960
Glu Lys Val Ser Gly Asp Tyr Gly His Pro Val Tyr Ile Val Gln Glu
280                 285                 290                 295

ATG CCC CCG CAG AGC CCG GCG AAC ATT TAC TAC AAG GTC TGA               1002
Met Pro Pro Gln Ser Pro Ala Asn Ile Tyr Tyr Lys Val
            300                 305
```

(2) INFORMATION FOR SEQ ID NO: 2:

(i) SEQUENCE CHARACTERISTICS:
        (A) LENGTH: 333 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Val Arg Arg Asp Ser Val Trp Lys Tyr Cys Trp Gly Val Leu
-25                 -20                 -15                 -10

Met Val Leu Cys Arg Thr Ala Ile Ser Lys Ser Ile Val Leu Glu Pro
            -5                   1                   5

Ile Tyr Trp Asn Ser Ser Asn Ser Lys Phe Leu Pro Gly Gln Gly Leu
            10                  15                  20

Val Leu Tyr Pro Gln Ile Gly Asp Lys Leu Asp Ile Cys Pro Lys
        25                  30                  35

Val Asp Ser Lys Thr Val Gly Gln Tyr Glu Tyr Tyr Lys Val Tyr Met
40                  45                  50                  55

Val Asp Lys Asp Gln Ala Asp Arg Cys Thr Ile Lys Lys Glu Asn Thr
            60                  65                  70

Pro Leu Leu Asn Cys Ala Lys Pro Asp Gln Asp Ile Lys Phe Thr Ile
            75                  80                  85

Lys Phe Gln Glu Phe Ser Pro Asn Leu Trp Gly Leu Glu Phe Gln Lys
            90                  95                  100
```

```
Asn Lys Asp Tyr Tyr Ile Ile Ser Thr Ser Asn Gly Ser Leu Glu Gly
    105                 110                 115

Leu Asp Asn Gln Glu Gly Gly Val Cys Gln Thr Arg Ala Met Lys Ile
120                 125                 130                 135

Leu Met Lys Val Gly Gln Asp Ala Ser Ser Ala Gly Ser Thr Arg Asn
                140                 145                 150

Lys Asp Pro Thr Arg Arg Pro Glu Leu Glu Ala Gly Thr Asn Gly Arg
                155                 160                 165

Ser Ser Thr Thr Ser Pro Phe Val Lys Pro Asn Pro Gly Ser Ser Thr
            170                 175                 180

Asp Gly Asn Ser Ala Gly His Ser Gly Asn Asn Ile Leu Gly Ser Glu
        185                 190                 195

Val Ala Leu Phe Ala Gly Ile Ala Ser Gly Cys Ile Ile Phe Ile Val
200                 205                 210                 215

Ile Ile Ile Thr Leu Val Val Leu Leu Leu Lys Tyr Arg Arg Arg His
                220                 225                 230

Arg Lys His Ser Pro Gln His Thr Thr Thr Leu Ser Leu Ser Thr Leu
            235                 240                 245

Ala Thr Pro Lys Arg Ser Gly Asn Asn Asn Gly Ser Glu Pro Ser Asp
        250                 255                 260

Ile Ile Ile Pro Leu Arg Thr Ala Asp Ser Val Phe Cys Pro His Tyr
    265                 270                 275

Glu Lys Val Ser Gly Asp Tyr Gly His Pro Val Tyr Ile Val Gln Glu
280                 285                 290                 295

Met Pro Pro Gln Ser Pro Ala Asn Ile Tyr Tyr Lys Val
                300                 305

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: FLAG peptide (xi) SEQUENCE DESCRIPTION: SEQ ID NO: 3:

Asp Tyr Lys Asp Asp Asp Asp Lys
1               5
```